(12) United States Patent
Blix

(10) Patent No.: US 8,088,100 B2
(45) Date of Patent: Jan. 3, 2012

(54) REINFORCED REWRAPPABLE BALLOON

(75) Inventor: John Blix, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 469 days.

(21) Appl. No.: 11/584,093

(22) Filed: Oct. 20, 2006

(65) Prior Publication Data

US 2008/0171977 A1    Jul. 17, 2008

(51) Int. Cl.
*A61M 29/00* (2006.01)

(52) U.S. Cl. .................................... 604/96.01

(58) Field of Classification Search ................ 604/96.01
See application file for complete search history.

(56) References Cited

U.S. PATENT DOCUMENTS

| | | | |
|---|---|---|---|
| 4,490,421 A | 12/1984 | Levy | 428/35 |
| 4,906,244 A | 3/1990 | Pinchuk et al. | 606/194 |
| 4,935,190 A | 6/1990 | Tennerstedt | 264/529 |
| 4,950,239 A | 8/1990 | Gahara et al. | 604/96 |
| 5,037,392 A | 8/1991 | Jillstead | 604/96 |
| 5,053,007 A | 10/1991 | Euteneuer | 604/96 |
| 5,087,246 A | 2/1992 | Smith | 604/96 |
| 5,147,302 A | 9/1992 | Euteneuer et al. | 604/103 |
| 5,163,989 A | 11/1992 | Campbell et al. | 65/110 |
| 5,209,799 A | 5/1993 | Vigil | 156/156 |
| 5,226,887 A * | 7/1993 | Farr et al. | 604/103.09 |
| 5,264,260 A | 11/1993 | Saab | 428/35.5 |
| 5,304,340 A | 4/1994 | Downey | 264/521 |
| 5,306,246 A | 4/1994 | Sahatjian et al. | 604/96 |
| 5,318,587 A | 6/1994 | Davey | 606/194 |
| 5,328,468 A | 7/1994 | Kaneko et al. | 604/96 |
| 5,342,307 A | 8/1994 | Euteneuer et al. | 604/103 |
| 5,344,400 A | 9/1994 | Kaneko et al. | 604/96 |
| 5,350,361 A | 9/1994 | Tsukashima et al. | 604/96 |
| 5,456,666 A | 10/1995 | Campbell et al. | 604/96 |
| 5,458,572 A | 10/1995 | Campbell et al. | 604/96 |
| 5,478,319 A | 12/1995 | Campbell et al. | 604/96 |
| 5,500,180 A | 3/1996 | Anderson et al. | 264/532 |
| 5,556,383 A | 9/1996 | Wang et al. | 604/96 |
| 5,714,110 A | 2/1998 | Wang et al. | 264/529 |
| 5,718,684 A | 2/1998 | Gupta | 604/96 |
| 5,746,745 A | 5/1998 | Abele et al. | 606/108 |
| 5,833,657 A | 11/1998 | Reinhardt et al. | 604/96 |
| 6,013,055 A * | 1/2000 | Bampos et al. | 604/103.07 |
| 6,033,380 A * | 3/2000 | Butaric et al. | 604/103.07 |
| 6,071,285 A | 6/2000 | Lashinski et al. | 606/108 |
| 6,126,652 A | 10/2000 | McLeod et al. | 606/1 |
| 6,146,356 A | 11/2000 | Wang et al. | 604/96 |

(Continued)

FOREIGN PATENT DOCUMENTS

EP    0565796    10/1993

(Continued)

*Primary Examiner* — Nicholas Lucchesi
*Assistant Examiner* — Jason Flick
(74) *Attorney, Agent, or Firm* — Vidas, Arrett & Steinkraus, P.A.

(57) ABSTRACT

A catheter system comprises a catheter and a reinforced catheter balloon. The catheter balloon has at least one cone portion and a working portion. The catheter balloon has in cross section the at least one cone portion has a polygonal shape with sides and corners. The balloon is disposed about a longitudinal axis and has an inflated state and an uninflated state. In the uninflated state the working portion of the balloon forms wings which have tips that are circumferentially aligned with the corners of the cone portion.

20 Claims, 7 Drawing Sheets

U.S. PATENT DOCUMENTS

| | | | |
|---|---|---|---|
| 6,242,063 B1 | 6/2001 | Ferrera et al. | 428/35.2 |
| 6,270,522 B1 | 8/2001 | Simhambhatla et al. | 623/1.11 |
| 6,283,743 B1 | 9/2001 | Traxler et al. | 425/391 |
| 6,284,333 B1 * | 9/2001 | Wang et al. | 428/35.5 |
| 6,491,711 B1 * | 12/2002 | Durcan | 606/194 |
| 6,572,813 B1 | 6/2003 | Zhang et al. | 264/519 |
| 6,596,219 B2 * | 7/2003 | Schaible et al. | 264/515 |
| 6,623,689 B2 | 9/2003 | Traxler et al. | 264/573 |
| 6,946,092 B1 | 9/2005 | Bertolino et al. | 264/512 |
| 6,988,881 B2 | 1/2006 | Motsenbocker et al. | 425/392 |
| 7,128,868 B2 | 10/2006 | Eidenschink | 264/442 |
| 2002/0163104 A1 | 11/2002 | Motsenbocker et al. | 264/320 |
| 2003/0083687 A1 | 5/2003 | Pallazza | 606/191 |
| 2003/0130717 A1 | 7/2003 | Hale et al. | 623/1.11 |
| 2003/0143350 A1 * | 7/2003 | Jimenez | 428/35.2 |
| 2003/0163157 A1 | 8/2003 | McMorrow et al. | 606/194 |
| 2005/0177130 A1 | 8/2005 | Konstantino et al. | 604/509 |
| 2005/0251194 A1 | 11/2005 | McHale | 606/192 |
| 2006/0015134 A1 | 1/2006 | Trinidad | 606/194 |
| 2007/0005092 A1 | 1/2007 | Godin et al. | 606/194 |

FOREIGN PATENT DOCUMENTS

| | | |
|---|---|---|
| WO | 9423787 | 10/1994 |
| WO | 9518647 | 7/1995 |
| WO | 9925417 | 5/1999 |

* cited by examiner

REINFORCED REWRAPPABLE BALLOON

CROSS-REFERENCE TO RELATED APPLICATIONS

Not Applicable

STATEMENT REGARDING FEDERALLY SPONSORED RESEARCH

Not Applicable

FIELD OF THE INVENTION

The present invention relates to the field of medical balloons, to catheters using such balloons, and methods of making and using the same.

BACKGROUND OF THE INVENTION

Various techniques or balloon constructions have been employed to facilitate the folding of the balloon about the balloon catheter in a uniform manner upon evacuation and deflation of the balloon after use.

One method employed to improve the refoldability of the balloon and improve withdrawal, has been to fold the balloon to form a number of wings. Prior to use, the balloon is typically folded or wrapped about the balloon catheter to fit within and pass through the guide catheter lumen. When inflation fluid is applied to the deflated balloon, the balloon wings or flaps unwrap and the balloon inflates to a fully expanded condition. When in the deflated state, the balloon collapses upon itself forming flaps or wings that must be folded or wrapped around the balloon catheter to allow it to be withdrawn from the patient's vasculature after use.

A number of approaches have been employed in forming a balloon that will refold into wings or flaps about the catheter shaft.

See, for example, U.S. Pat. Nos. 5,226,887, 5,318,587, 5,456,666 and 5,478,319 for various methods of improving balloon collapsibility after inflation. The entire content of these patents is hereby incorporated by reference herein.

The ability to withstand high inflation pressures and yet be compatible with small sheath sizes are major factors in developing reinforced and multi-layer balloon designs. There remains a need, however, for innovative and improved rewrappable reinforced balloons.

The art referred to and/or described above is not intended to constitute an admission that any patent, publication or other information referred to herein is "prior art" with respect to this invention.

All US patents and applications and all other published documents mentioned anywhere in this application are incorporated herein by reference in their entirety.

Without limiting the scope of the invention a brief summary of the claimed embodiments of the invention is set forth below. Additional details of the summarized embodiments of the invention and/or additional embodiments of the invention may be found in the Detailed Description of the Invention below.

SUMMARY OF THE INVENTION

The present invention relates to an improved rewrappable reinforced balloon and balloon catheter to reduce withdrawal force.

In at least one embodiment, the catheter system includes a catheter and a reinforced catheter balloon wherein in cross-section the cone portion has a polygonal shape when both inflated and deflated. Here the term cone is not strictly descriptive of a geometric state as the cone has a polygonal cross-section. Throughout the application a polygonal shape in cross-section can be descriptive of the cross-section of the inner surface of the balloon, the outer surface of the balloon, or both. In an uninflated state, the working portion of the balloon forms wings having tips which are substantially aligned with the corners of the polygonally shaped cone portion. In the inflated state, the working portion can be of a substantially circular or polygonal shape. Throughout the application a "circular" shape can include a substantially oval shape and/or any curved closed shape including any elliptical shape of any eccentricity including zero.

The wings can wrap or fold over one another when the balloon is fully deflated in order to minimize the profile of the balloon upon withdrawal of the catheter. Throughout the application, wings that "wrap over" or "fold over" indicate wings wherein a portion of one wing is rotated or moved about a longitudinal axis of the balloon such that it is radially disposed about a portion of another wing and reduces the profile of the balloon. Such a design also prevents pancaking of the balloon upon deflation. The term "deflated" may refer to a medical balloon which has been partially or fully evacuated of its inflation media or deflated from an inflated state, the inflated state being the state wherein the interior of the balloon has a pressure greater than that outside the balloon. Of course, a balloon may also be deflated from its fully expanded state, but remains in a state of expansion.

The balloon can be reinforced with reinforcement material such as strengthening fibers. The addition of the strengthening fibers to the polymer material can provide additional burst strength to the balloon. The reinforcement material may comprise various types of continuous or intermittent reinforcing components used in the composites of this invention. Among such suitable materials are continuous fiber or filament forms such as polyester, polyamide or carbon fiber, and further may be sphere and particulate forms such as glass. Reinforcing material may comprise glass, carbon, ceramic, fluoropolymer, graphite, liquid crystal polymers, polyester, polyamide, stainless steel, titanium and other metals such as nitinol, or radiopaque materials (such as Bismuth or Tungsten) and the like.

The continuous reinforcement may be used in filamentary form or it may be employed in the form of a yarn or as a fabric of plain weave, satin weave, twill weave, basket weave, braid, winding or the like. The composite structure may comprise parallel aligned continuous filaments extending within or along the inner or outermost dimension of the structure, the fibers being bonded together with the above-described thermoplastic polyimide which intimately contacts substantially the whole of the surfaces of the filaments.

Fibers can be embedded or layered onto the polymer matrix of the balloon and oriented longitudinally. The fibers can be distributed evenly throughout the balloon thereby reinforcing the entire balloon. In some embodiments, the fibers are concentrated in regions of the balloon. In some embodiments the fibers are disposed on the balloon only at the corners to reinforce the corners and assist in the formation of wings when uninflated. In some embodiments, the balloon includes fibers which are of a nano-tube material. In some embodiments the reinforced catheter balloon is formed from a polymer blend which includes liquid crystal polymer.

In some embodiments, the catheter balloon includes a tube-in-tube design, a layer-by-layer design, or both.

The balloon may be set into any geometric shape desired including, for example, a two wing, three wing, four wing structure, a star structure, i.e. typically having five or more points, triangle, rectangle, square, etc. In some embodiments the wings could form a T-shape.

The present invention can be employed for balloon angioplasty and/or for balloons used in stent delivery systems.

These and other aspects, embodiments and advantages of the present invention will become immediately apparent to those of ordinary skill in the art upon review of the Detailed Description and Claims to follow.

BRIEF DESCRIPTION OF THE SEVERAL VIEWS OF THE DRAWING(S)

A detailed description of the invention is hereafter described with specific reference being made to the drawings.

FIG. 1 is a side view of a catheter balloon.

FIGS. 2a-h are cross-sectional views of the cone portion of a catheter balloon.

FIG. 3 is a cross-sectional view of the working portion of a catheter balloon in an expanded state.

FIGS. 3a-c are cross-sectional views of the working portion of FIG. 3 in a deflated or uninflated, unwrapped state.

FIGS. 5a-h are cross-sectional views of the shapes of both the cone portion and the working portion of a catheter balloon.

Figure 6A:
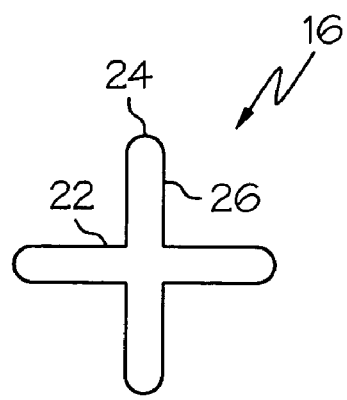
Figure 6B:
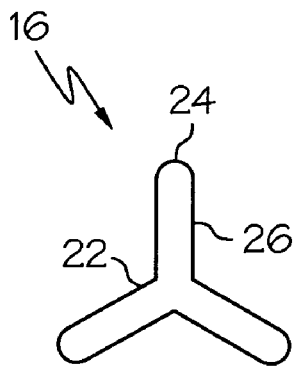
Figure 6C:
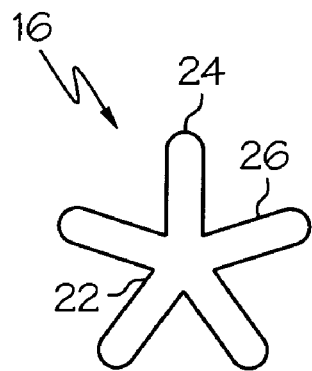

FIGS. 6a-6c are cross-sectional views of the polygonal working portion of a catheter balloon in a deflated or uninflated, unwrapped state.

Figure 6D:
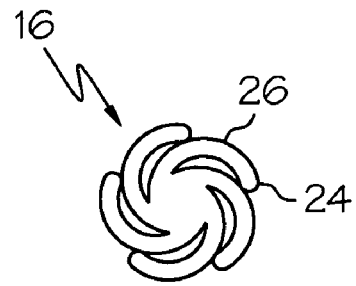

FIG. 6d is a cross-sectional view of the working portion of the catheter balloon of FIG. 6a in a deflated or uninflated, wrapped state.

Figure 7A:
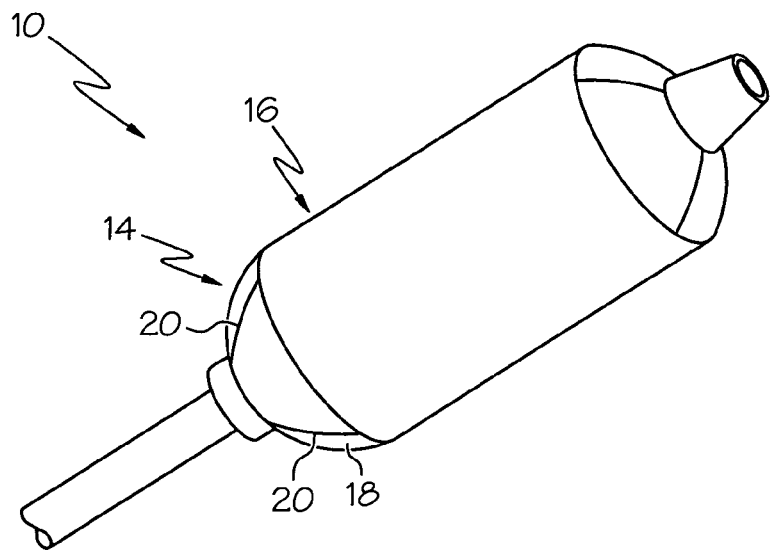

FIG. 7a is a perspective view of a catheter balloon having polygonal cone portions.

Figure 7B:
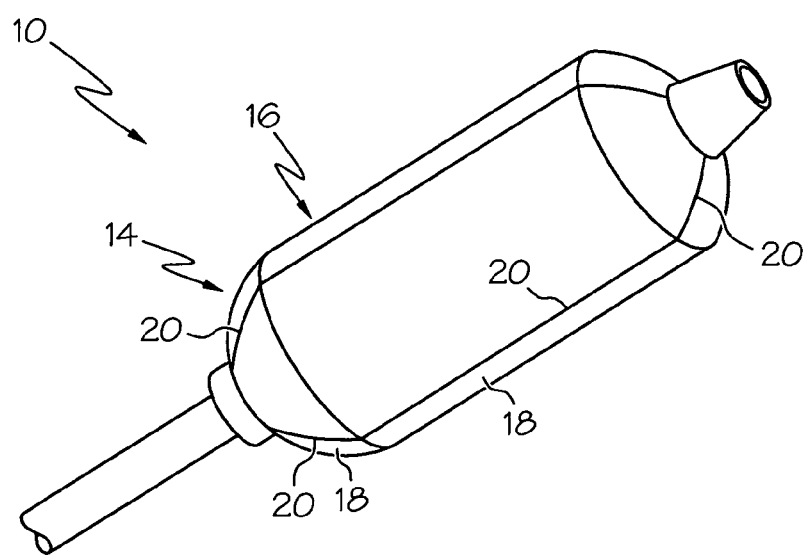

FIG. 7b is a perspective view of a catheter balloon having polygonal cone portion and working portion.

Figure 8A:
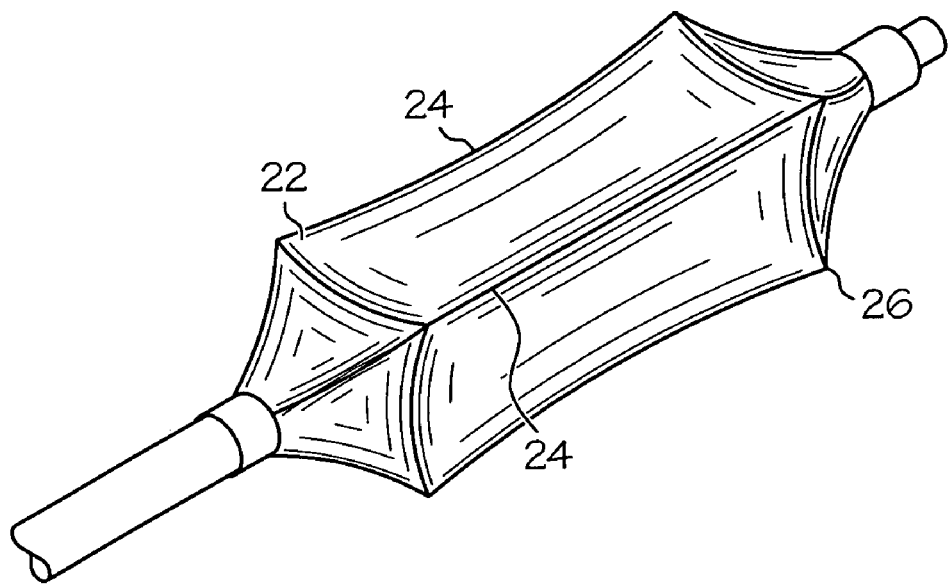

FIG. 8a is a perspective view of a deflated and unwrapped catheter balloon.

Figure 8B:
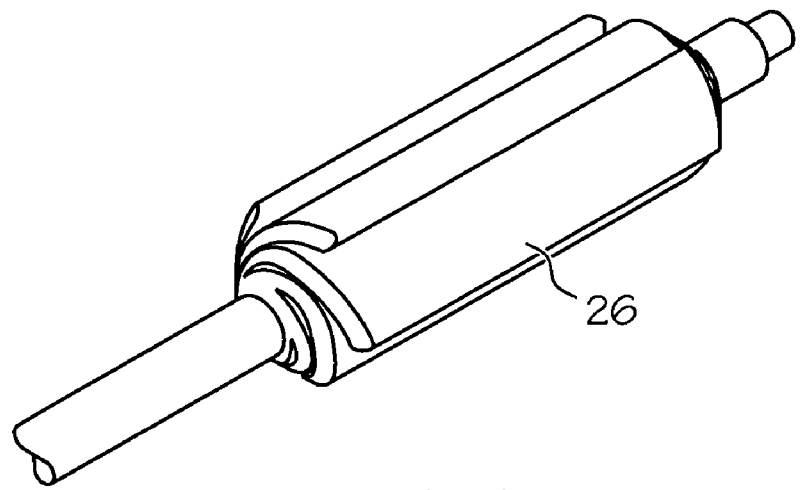

FIG. 8b is a perspective view of a fully deflated catheter balloon in a wrapped condition.

Figure 9A:
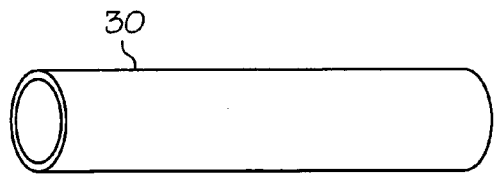
Figure 9B:
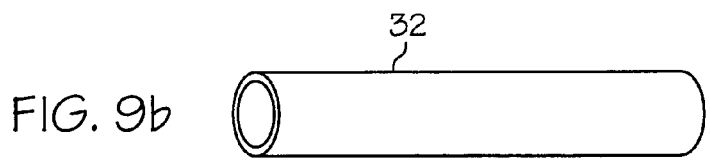

FIG. 9a-b are perspective views of tubes used in forming a catheter balloon.

Figure 5A:
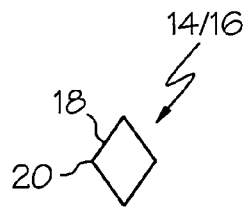
Figure 5B:
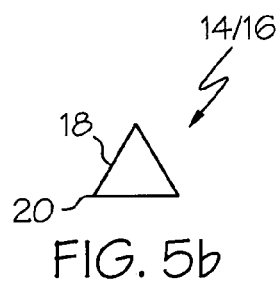
Figure 5C:
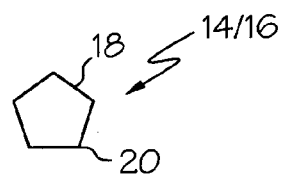
Figure 5D:
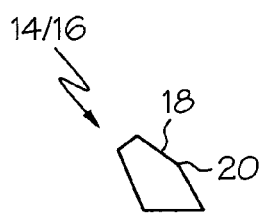
Figure 5E:
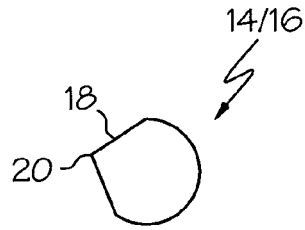
Figure 9C:
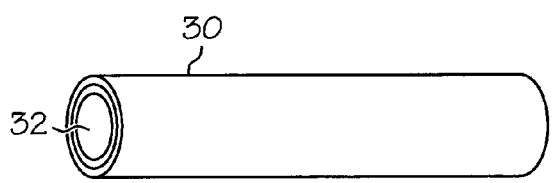

FIG. 9c is a perspective view of the tubes of FIGS. 5a-b coaxially combined before being formed into a catheter balloon.

Figure 10:
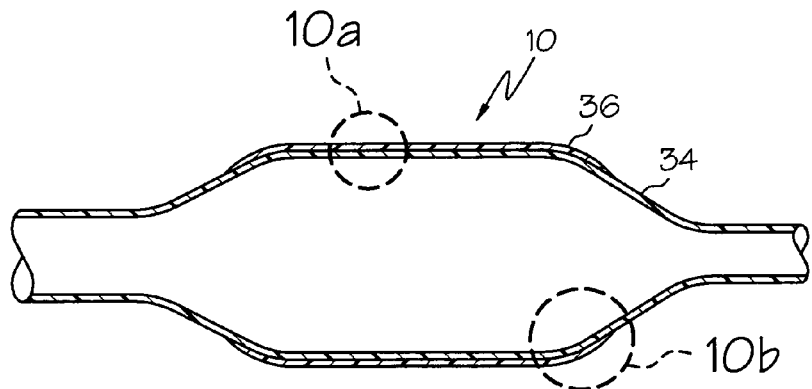

FIG. 10 is a cross-sectional side view of a layered catheter balloon.

Figure 10A:
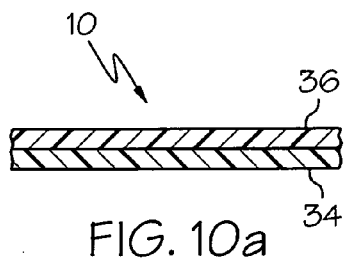
Figure 10B:
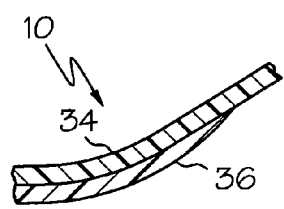

FIGS. 10a-b are cross-sectional side views of portions of the balloon of FIG. 10.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, unless otherwise indicated, identical reference numerals used in different figures refer to the same component.

The expandable balloons according to the invention are expandable from a folded configuration for insertion into a patient's body lumen, expanded to an enlarged diameter to provide medical treatment, with a fluid, for example, and after treatment, being evacuated and deflated wherein the balloon is revertible into a folded configuration of a predetermined shape.

The selected inflation pressures to expand the balloon to its enlarged diameter may vary depending on the type of balloon employed, the application for which the balloon is employed, the type of balloon material employed, the wall thickness, number of layers employed, and whether or not there is a reinforcement material such as fibers or braids employed, etc. Reinforcement materials can increase balloon inflation pressures. Suitable inflation pressures may range from about 8 to about 30 atmospheres.

Balloons typically have a rated burst pressure which is defined as some pressure below that of the actual burst pressure of a balloon. Rated burst pressure is also dictated by repeat inflation performance. Rated burst pressure is a term known in the art. Balloons employed in peripheral vessels, for example, may have rated burst pressures of about 12-14 atmospheres while balloons used in the coronary vessels may have burst pressures of about 18-21 atmospheres. These examples are intended for illustrative purposes only, and not as a limitation on the scope of the present invention. Modifying the design of the balloon, such as with reinforcement, for example braiding, may lead to higher rated burst pressures.

Balloons are typically formed by expanding a segment of extruded polymer tubing into a balloon mold. Balloon formation is described, for example, in U.S. Pat. Nos. 4,490,421, 5,264,260, 4,906,244, 4,935,190, 5,304,340, 5,306,246, 5,328,468, 4,950,239, 5,500,180, 5,556,383, 5,714,110, 6,146,356, 6,270,522, 5,344,400, 5,833,657, 6,572,813 and 6,946,092 each of which is incorporated by reference herein in their entirety.

The present invention relates to a reinforced balloon with improved refoldability after inflation.

While the expandable balloons described herein may take on many geometric configurations, there will be described herein, some specific embodiments of the invention.

Figure 1:
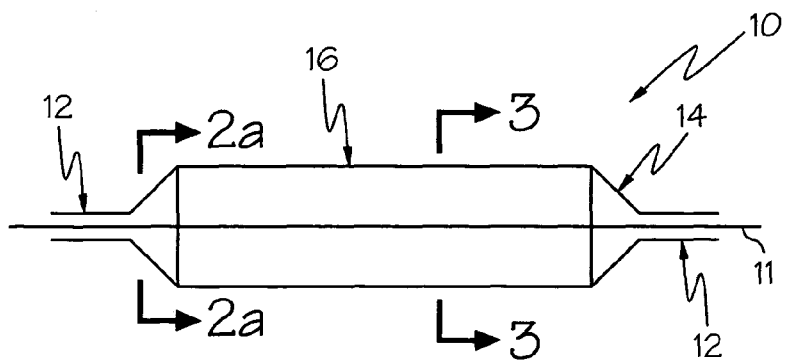
Figure 2A:
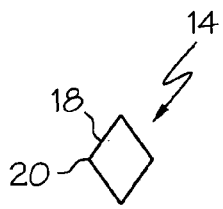
Figure 2B:
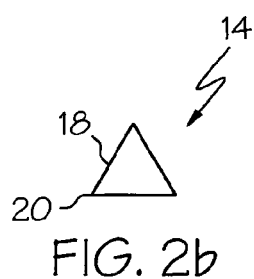
Figure 2C:
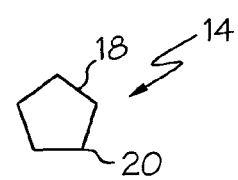
Figure 2D:
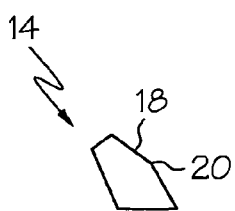
Figure 2E:
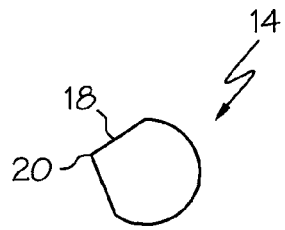

Turning now to the figures, FIG. 1 illustrates generally at 10, a side view of a balloon in an inflated state. Balloon 10 is disposed about longitudinal axis 11 and has waist portions 12, cone portions 14, and a working portion 16. Fluid can be supplied to the balloon 10 to expand the balloon, and upon negative pressure, the balloon can be deflated. In FIGS. 2a-c embodiments of the cone portion 14 of balloon 10 are shown in an inflated state at cross sectional view 2A-2A. As illustrated, in cross-section the cone portion has a substantially-regular polygonal shape including polygons having 3, 4, and 5 sided polygons with sides 18 and corners 20. It should be noted that the polygon can have any number of sides. The sides are generally straight though the sides in some embodiments include a curve. The cone portion can also have corners 20 with substantially different angles between the sides forming the corner and can also have sides 18 with substantially different lengths such that the cone cross-sections are substantially irregularly polygon shaped as illustrated in FIG. 2d. In some embodiments the polygonal shape of the cone 14 does extended over the full longitudinal length of the cone. In other embodiments and as shown in FIG. 2e, the cone 14 has a construction in a circumferential direction such that one portion has corners 20 and sides 18 and another portion (e.g. a semi-circle) longitudinally aligned has a circular shape.

Figure 2F:
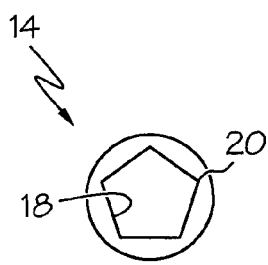
Figure 2G:
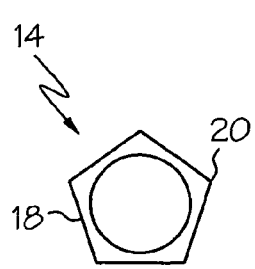
Figure 2H:
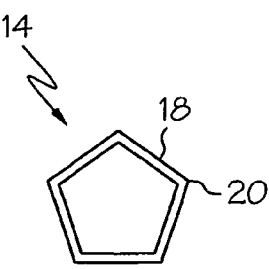

It should be noted that the balloon walls have a width between the interior surface and the exterior surface. Though many polygonal shapes are used for the cone portion of this invention, FIGS. 2f-2h illustrate a 5-sided polygon shape that presents the concept that in different embodiments the polygonal cross-sectional shape can be on the interior surface, the exterior surface, or both.

Figure 3:
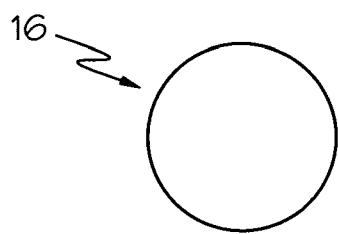
FIG. 3d is a cross-sectional view of the working portion of the catheter balloon of FIG. 3a in a deflated or uninflated, wrapped state.
Figure 3A:
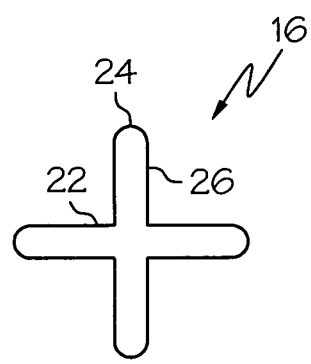
Figure 3B:
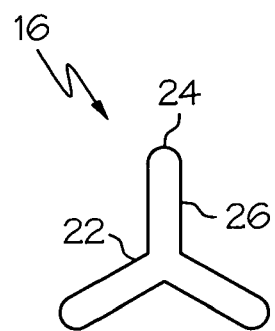
Figure 3C:
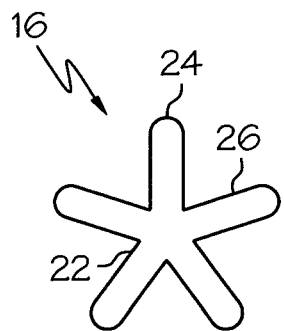

In some embodiments the working portion 16 has a substantially circular cross-sectional shape as shown in FIG. 3 when in an inflated state. In some embodiments, as shown in FIGS. 3a-3c, the working portions in an uninflated state have collapsed portions 22 which are more apt to collapse than tip portions 24 upon deflation of the balloon. In at least one embodiment, the tip portions 24 are substantially circumferentially aligned with the corners 20 of the cone portions 14. The corners 20 of the cone portion 14 can collapse less quickly than the other portions of the cone portion upon deflation thus resulting in the tip portions of the working portion. However, it should be noted that in some embodiments the tip portions are substantially circumferentially aligned with portions of the sides 18.

Figure 3D:
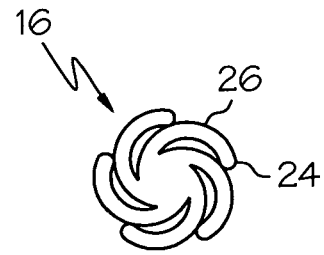

The collapsed portions 22 and the tip portions 24 form wings 26 which can then fold or wrap upon one another when more fully deflated as illustrated in FIG. 3d. The wrapped wings can extend about the catheter for over 360 degrees such that the tip portions 24 of a wing 26 wraps about its own base portion. Depending upon the length of the wings and the diameter of the catheter shaft, the degrees of wrapping can be increased or decreased. In order to maintain as small a profile as possible the wing is smoothly wrapped about the catheter without bunching or pancaking. Any conventional balloon folding apparatuses and techniques may be employed in folding or wrapping the balloons according to the invention. Conventional technologies typically employ a number of hard die-like structures which are moved radially inward toward the center of a partially expanded balloon. Negative pressure can be applied to the balloon, such as by vacuum, to assist during the folding process. The balloon is typically placed in a holding fixture, and then maintained in a partially expanded state until the dies have reached the end of their stroke. A vacuum is then applied to deflate the balloon and form wings that conform to the configuration of the dies. The wings may then be wrapped or rolled about the circumference of the balloon. For a three wing apparatus, the dies of the folding apparatus may be circumferentially spaced at 60 degree intervals about the balloon. Examples of balloon folding apparatuses are found in commonly assigned U.S. Patent Publication Nos. 2003/083687 and 2003/0163157, the entire contents of which are incorporated by reference herein. Other examples include U.S. Pat. Nos. 5,350,361, 6,126,652, 6,033,380 and 2002/163104, each of which is incorporated by reference herein in their entirety. Wings may also have other than a triangular shape. See, for example, commonly assigned U.S. Patent Publication No. 2006/0015134, the entire content of which is incorporated by reference herein.

Figure 4:
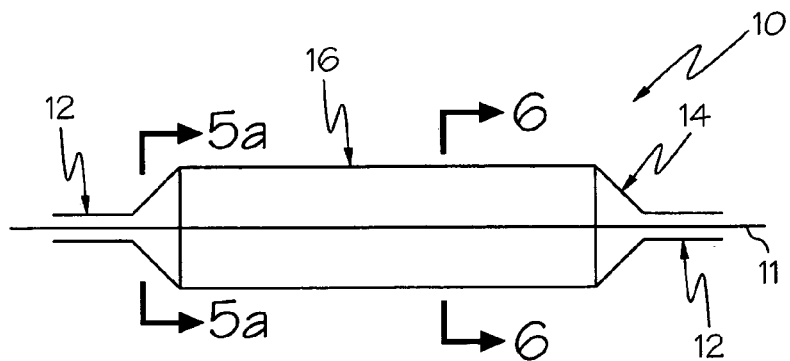
FIG. 4 is a side view of a balloon.

In some embodiments as shown in FIG. 4, the balloon 10 has a working portion 16 with the substantially same geometric shape in cross-section as that of the cone portion 14. It should be noted that the cross-section of the working portion 16 at 3-3 will be larger than that of the cone portion 14 at cross-sectional view 2A-2A. As such, in an expanded state, the cone portion 14 and the working portion 16 can have the substantially same cross-sectional shape as shown in FIGS. 5a-e, but they would be of different sizes. In some embodiments the cone portions and the working portion can have portions that are similarly sized.

Figure 5F:
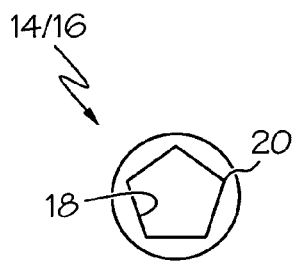
Figure 5G:
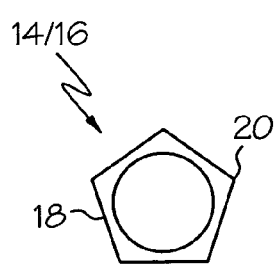
Figure 5H:
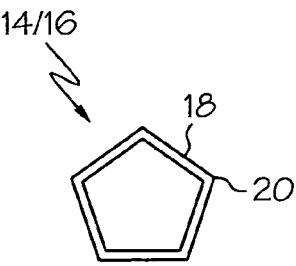

It should be noted that the balloon cone walls and the balloon working portion wall have an interior surface and an exterior surface. Though many polygonal shapes are used for the cone portion 14 and working portion 16 of this invention, FIGS. 5f-5h illustrate a 5-sided polygon shape that presents the concept that in some embodiments the polygonal cross-sectional shape can be on the interior surface, the exterior surface, or both.

In a deflated state the working portion 16 can have cross-sectional shapes as those shown in FIGS. 6a-c. The working portion can have wings 26 formed from collapsed portions 22 and tip portions 24. The tip portions can coincide with the corners 20 of FIGS. 5a-e. The shapes provided in the figures are only used to illustrate embodiments of the invention as the cross-section can be any polygonal shape, regular or irregular. It should be noted that in some embodiments the tip portions coincide with portions of the sides 18.

For purposes of further illustrating an embodiment of the invention, a balloon 10 in the expanded state having a working portion 16 and cone portion 14 having a shape as in FIG. 5a can have an uninflated state as shown in FIG. 6a. Upon further deflation the working portion 16 of the balloon 10 can have a fully deflated state as illustrated in FIG. 6d wherein the wings 26 fold or wrap about one another. It should be noted that this example is intended for illustration and that many other shapes can be deflated as in the example and that in some embodiments the wings 26 can be wrapped more tightly or loosely than is shown in FIG. 6d.

In FIG. 7a a perspective view of an expanded balloon 10 having a circular working portion 16 and a polygonal cone portion 14 is shown. In FIG. 7a the balloon 10 has more walls 18 than that of FIG. 4. In FIG. 7b the working portion 16 and the cone portion 14 have a polygonal shape in the expanded state.

In FIG. 8a a balloon 10 is shown in a deflated state wherein the collapsed portions 22 and tip portions 24 have formed wings 26. The balloon 10 as shown can be of the type having a circular working portion 16 or a polygonal working portion when in the inflated state. Upon further deflation the wings 26 can be wrapped around the catheter as illustrated in FIG. 8b.

The ability to withstand high inflation pressures and yet have compatibility with small sheath sizes is a major factor in developing balloons which are reinforced, multi-layer, or both.

In additional embodiments the foldable balloon can be constructed of multiple layers that have similar or different material properties. The multiple layers can provide greater reinforcement than a single layer. In some embodiments at least one layer includes reinforcement material therein. In some embodiments, such as tube-in-tube design, parisons or tubes 30, 32 are formed (e.g. by extrusion) as shown in FIGS. 9a and 9b. Once the first and second parisons are formed, one of each are coaxially disposed in overlapping relationship as shown in FIG. 9c so that the first tubular parison surrounds the second. While the process thus far described contemplates only two coaxially disposed tubular parisons, those skilled in the art can appreciate that the method can be extended to three or more layers by merely creating additional tubular parisons of an appropriate size so that they can be telescopingly disposed relative to one another in a predetermined order. For example, if the polymeric materials chosen for the first and second tubular parisons tend not to bond well to one another, a third parison, compatible with each, can be formed and dimensioned so as to fit between the outermost and innermost parisons when the three are telescopingly disposed relative to one another. The multiple tube parison can then shaped into a catheter balloon.

An alternate embodiment of the invention with respect to balloon construction may comprise a multiple layer or layer-by-layer balloon 10 of the type shown in FIGS. 10 and 10a-

10b. The balloon 10 can be comprised of a blow molded balloon of thermoplastic polyimide having a deposited outer layer 36 of prior art thermoset polyimide, polyamide, or any other material laid down in the known manner on the inflated thermoplastic polyimide 34 of the balloon. Such construction provides a balloon having predominantly longitudinal burst characteristics. Strengthening fiber materials can also be included in the outer layer 36 and/or the inner layer 34. This embodiment also offers one the opportunity of tailoring the compliance characteristics of the balloon by selectively altering the number, arrangement and thickness of these layers in a variety of configurations. Moreover, the thermoplastic polyimide balloons of the invention may have no outer layer at all or they may carry a single outer layer or multiple outer layers (fill or partial) of extruded thermoplastic polyimide or other polymer materials for layer 36.

In manufacturing the balloons of the invention, techniques and tools utilized in the prior art for thermoplastic balloons are readily adaptable. The balloons according to the invention may be formed at least in part from any suitable balloon material. Suitable classes of materials include, but are not limited to, polyolefins, polyamides (i.e. nylons), polyesters and copolyesters, polyurethanes, polyethers, polyimides, polycarbonates, etc. Copolymers are suitable for use as well.

Examples of suitable polyesters include, but are not limited to, polyethylene terephthalate (PET), polybutylene terephthalate (PBT), polyethylene naphthalate (PEN), etc.

HYTREL®, polyester-ester elastomers available from DuPont Wilmington, Del. and ARNITEL® polyester-esters and polyether-esters available from DSM Engineering Plastics—Americas in Evansville, Ind. may also be employed herein. These polymers are available in different grades depending on desired balloon properties.

Block copolymer elastomers, such as poly(ether-block-amide) block copolymers available under the tradename of PEBAX® from Arkema in Paris, France, may be employed herein. PEBAX® is available in different grades, for example, 6333, 7033 and 7233 are all suitable depending on the balloon properties desired.

Suitable polyamides include, but are not limited to, nylon 6, nylon 10, nylon 11 and nylon 12.

Polyurethanes are available commercially under the tradenames of ISOPLAST® and PELLETHANE® from Dow Chemical Co. in Midland, Mich.

These and other suitable balloon materials are described in U.S. Pat. Nos. 4,906,244, 5,556,383 and 6,270,522, the entire contents of which are incorporated by reference herein. The present invention is not limited by the polymeric material which may be employed herein.

Reinforcement materials such as liquid crystal polymers may also be employed herein. Liquid crystal polymers are described for use in balloons in U.S. Pat. Nos. 6,242,063, 6,284,333 and 6,596,219, the entire contents of which are incorporated by reference herein.

The above lists are intended for illustrative purposes only, and not intended to limit the scope of the present invention. Selection of balloon materials is known to those of skill in the art.

The above examples and disclosure are intended to be illustrative and not exhaustive. These examples and description will suggest many variations and alternatives to one of ordinary skill in this art. All these alternative and variations are intended to be included within the scope of the claims, where the term "comprising" means "including, but not limited to." Those familiar with the art may recognize other equivalents to the specific embodiments described herein which equivalents are also intended to be encompassed by the claims.

The invention claimed is:

1. A catheter system comprising a catheter and a catheter balloon, the catheter balloon having at least one waist portion, at least one cone portion having an inner surface and an outer surface, and a working portion, the at least one cone portion extending from the working portion to the at least one waist portion, the catheter balloon being disposed about a longitudinal axis and having an inflated state and an uninflated state, the outer surface of the at least one cone portion having a polygonal shape in cross-section and the inner surface having circular shape in cross-section, the polygonal shape is a three, four or five sided polygon that extends over the entire length of the cone, and the working portion having a circular shape in cross-section, in cross-section the at least one cone portion including sides which intersect to define corners, in the uninflated state the working portion of the balloon comprising wings, each of the wings having a tip which is substantially circumferentially aligned with one of the corners of the conical portion.

2. The catheter system of claim 1, wherein in a deflated state the wings are folded over one another.

3. The catheter system of claim 1, wherein the at least one cone portion has a regular polygon shape in cross-section.

4. The catheter system of claim 1 having two cone portions.

5. The catheter system of claim 1 wherein the catheter balloon is a reinforced catheter balloon comprising a polymer matrix having strengthening fibers.

6. The catheter system of claim 5 wherein the strengthening fibers include a liquid crystal polymer.

7. The catheter system of claim 5 wherein the fibers are embedded within the polymer matrix.

8. The catheter system of claim 5 wherein the fibers include nano-tube fiber material.

9. The catheter system of claim 1 wherein the catheter balloon includes a tube-in-tube construction.

10. The catheter system of claim 1 wherein the catheter balloon includes a layer-by-layer design.

11. A catheter system comprising a catheter and a catheter balloon, the catheter balloon having at least one waist portion, at least one cone portion and a working portion, the catheter balloon having an inner surface and an outer surface, the catheter balloon is formed from a first polymer layer, the catheter balloon comprising a second polymer layer deposited on the first polymer layer and extending over the body portion and partially over the cone portion, the at least one cone portion extending from the working portion to the at least one waist portion, the catheter balloon being disposed about a longitudinal axis and having an inflated state and an uninflated state, the working portion and the at least one cone portion having a convex polygonal shape in cross-section, the convex polygonal shape extends the entire length of the cone portion, the outer surface of the at least one cone portion including sides which intersect to define corners, in the uninflated state the working portion of the balloon comprising wings, each wing having a tip extending from one of the corners of the cone portion over the length of the working portion, in a fully deflated state the wings wrap about one another, the tip is circumferentially aligned with the corners of the cone portion.

12. The catheter system of claim 11, wherein the at least one cone portion has a regular polygon shape in cross-section.

13. The catheter system of claim 11 having two cone portions.

14. The catheter system of claim 11 wherein the catheter balloon is a reinforced catheter balloon comprising a polymer matrix having strengthening fibers.

15. The catheter system of claim 14 wherein the catheter balloon comprises a polymer blend which includes a liquid crystal polymer.

16. The catheter system of claim 14 wherein the fibers are embedded within the polymer matrix.

17. The catheter system of claim 14 wherein the fibers includes nano-tube fiber material.

18. The catheter system of claim 11 wherein the catheter balloon includes a tube-in-tube design.

19. The catheter system of claim 11 wherein the catheter balloon includes a layer-by-layer design.

20. A catheter system comprising a catheter and a catheter balloon, the catheter balloon having at least one cone portion and a working portion, the catheter balloon comprising an inner surface and an outer surface with a wall extending there between, the balloon being disposed about a longitudinal axis and having an inflated state and an uninflated state, in the inflated state the at least one cone portion having a polygonal shape in cross-section, the polygonal shape is a four or five sided polygon that extends over the entire length of the cone, and the working portion having a circular shape in cross-section, the inner surface and the outer surface of the at least one cone portion including sides which intersect to define corners, the catheter balloon comprising a strengthening fiber material embedded within a polymer matrix, in the uninflated state the working portion of the balloon comprising wings, each wing having a tip extending from one corner of the cone portion over the length of the working portion, in a fully deflated state the wings wrapped about one another.

* * * * *